US012781280B2

(12) United States Patent
Alsheimer

(10) Patent No.: US 12,781,280 B2
(45) **Date of Patent: *Nov. 3, 2026**

(54) MARKER AND METHOD FOR ANALYSING BIOLOGICAL SAMPLES

(71) Applicant: LEICA MICROSYSTEMS CMS GMBH, Wetzlar (DE)

(72) Inventor: Soeren Alsheimer, Wetzlar (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 525 days.

This patent is subject to a terminal disclaimer.

(21) Appl. No.: 18/452,628

(22) Filed: Aug. 21, 2023

(65) Prior Publication Data

US 2024/0068028 A1 Feb. 29, 2024

(30) Foreign Application Priority Data

Aug. 23, 2022 (EP) .................................... 22191689

(51) Int. Cl.
*C12Q 1/6876* (2018.01)

(52) U.S. Cl.
CPC ................................. *C12Q 1/6876* (2013.01)

(58) Field of Classification Search
CPC ....... C12Q 1/6876; C12Q 1/68; C12Q 1/6816
See application file for complete search history.

(56) References Cited

U.S. PATENT DOCUMENTS 12,347,527 B2 * 7/2025 Bradl ..................... G16B 50/30
2014/0057805 A1 2/2014 Tinnefeld et al.
2016/0271268 A1 9/2016 Shih et al.

FOREIGN PATENT DOCUMENTS

WO WO 2019/222178 A1 11/2019
WO WO PCT/EP2021/058785 A1 4/2021
WO WO 2022/207125 A1 10/2022
WO WO 2022/242887 A1 11/2022

OTHER PUBLICATIONS

Alberts et al., "The Structure and Function of DNA", Molecular Biology of the Cell, 4th Edition, pp. 1-7 (print out). (Year: 2002).*

(Continued)

*Primary Examiner* — Young J Kim
(74) *Attorney, Agent, or Firm* — LEYDIG, VOIT & MAYER, LTD.

(57) ABSTRACT

A marker for marking a biological sample or a discrete entity including the biological sample includes an oligonucleotide nanostructure backbone with a plurality of attachment sites at predetermined positions, a plurality of labels for attachment to at least one of the attachment sites, and at least a first orientation indicator and a second orientation indicator. Each label includes at least one dye, an encoding oligonucleotide portion configured to encode characteristics of the at least one dye, and an attachment oligonucleotide portion configured to reversibly attach to one of the attachment sites. The attachment oligonucleotide portion of each label includes a unique oligonucleotide sequence configured to bind to a complementary sequence of one of the attachment sites.

16 Claims, 10 Drawing Sheets

(56) References Cited

OTHER PUBLICATIONS

Vanhorn, Sadie and Samantha A. Morris: "Next-Generation Lineage Tracing and Fate Mapping to Interrogate Development", Developmental Cell 56, CellPress, US, Oct. 21, 2020, pp. 7-21.
Duncombe, Todd A. and Petra S Dittrich: "Droplet barcoding: tracking mobile micro-reactors for high-throughput biology", Current Opinion in Biotechnology, Elsevier, Netherlands, Jun. 12, 2019, pp. 205-212.
Lawson, Michael and Johan Elf: "Imaging-based screens of pool-synthesized cell libraries", Nature Methods, vol. 18, Apr. 2021, Nature Portfolio, UK, pp. 358-365.
Barbara Sacca et al., "DNA Origami: The Art of Folding DNA," Angewandte Chemie International Edition, Dec. 7, 2011, pp. 58-66, vol. 51, Issue 1, Wiley-VCH Verlag Gmbh & Co. KGaA, Weinheim, Germany.
Paul W. K. Rothemund, "Folding DNA to create nanoscale shapes and patterns," Nature, Mar. 16, 2006, pp. 297-302, 440, Nature Publishing Groups, Berlin, Germany.

* cited by examiner

MARKER AND METHOD FOR ANALYSING BIOLOGICAL SAMPLES

CROSS REFERENCE TO RELATED APPLICATIONS

This application claims benefit to European Patent Application No. EP 22191689.3, filed on Aug. 23, 2022, which is hereby incorporated by reference herein.

FIELD

The present invention relates to a marker and method for marking biological samples or discrete entities comprising the biological sample.

BACKGROUND

The human body contains several hundred terminally different cell types such as muscle cells, enterocytes, and Purkinje neurons for example which basically share the same genome but exhibit strikingly different phenotypes. Ultimately these phenotypes are related to molecular interactions inside these cells between different classes of molecules such as the genome (DNA), the transcriptome (RNA), the proteome (protein), etc.

Single cell RNA sequencing and other single multi-omics technologies have followed the advent of next generation sequencing platforms and allow to make massively parallel measurements of these data layers measuring hundreds, thousands or even "genome-wide" (approx. 20,000 protein coding genes). These methods are collectively referred to as multi-omics. While these measurements are very useful to map the transcriptional cell state space and increasingly provide access to other data layers at scale, they rely on dissociating tissue into suspensions of cells. Tissue dissociation, however, removes cells from their surrounding taking away the auto-, para-, and juxtracrine signalling inputs as well as severing the attachment of the cell to the extracellular matrix and as such has profound impact on the cell. A cell in suspension may immediately round and no longer display a normal cell morphology. These changes also impact the various molecular layers described above.

This drawback has fuelled interest in technologies that can similarly perform multi-omics characterization, but in the tissue context. The currently available technologies include protein multiplexing, MIBI/IMC, various single-molecule FISH-based methods (e.g. MERFISH, SeqFISH), and spatial profiling methods such as the Visium platform from 10× Genomics or Nanostring's GeoMx. Neither of the aforementioned methods can measure the whole transcriptome at the single level within a tissue section as either the plexing or the spatial resolution is not high enough.

SUMMARY

In an embodiment, the present disclosure provides a marker for marking a biological sample or a discrete entity including the biological sample. The marker includes an oligonucleotide nanostructure backbone with a plurality of attachment sites at predetermined positions, a plurality of labels for attachment to at least one of the attachment sites, and at least a first orientation indicator and a second orientation indicator. Each label includes at least one dye, an encoding oligonucleotide portion configured to encode characteristics of the at least one dye, and an attachment oligonucleotide portion configured to reversibly attach to one of the attachment sites. The attachment oligonucleotide portion of each label includes a unique oligonucleotide sequence configured to bind to a complementary sequence of one of the attachment sites.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
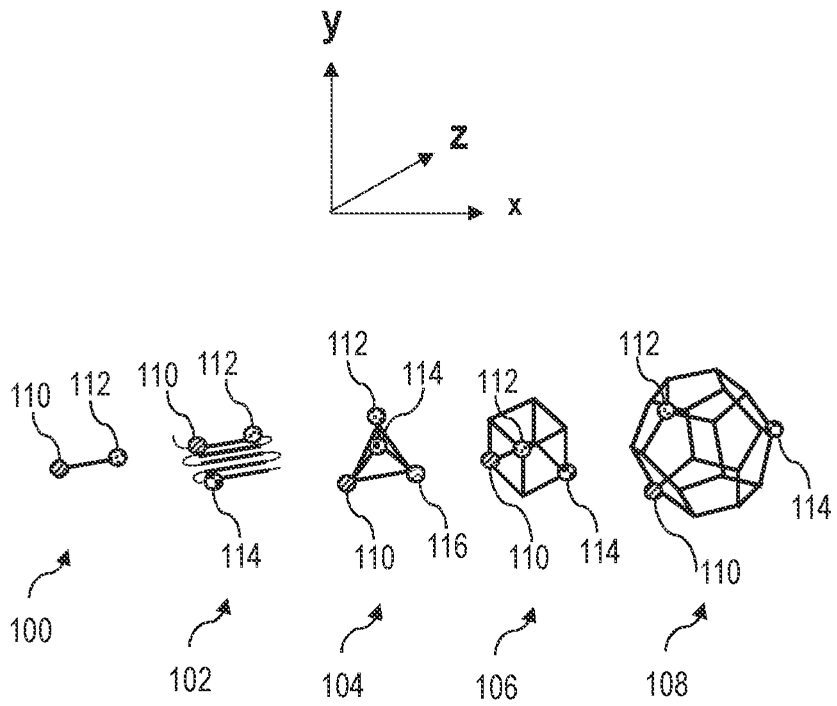
FIG. 1 shows several nanostructure backbones with orientation indicators.

Embodiments of the present invention can provide a marker and a method that enable tracking biological samples between different types of analyses in an efficient and fast way.

Embodiments of the present invention can overcome the limitations and provide a means to connect the cellular phenotypes with multi-omics in particular single cell RNA seq and ATAC seq measurements. Embodiments of the present invention can also use markers that are compatible with tissue samples or cell suspension samples or particle suspension samples to mark and analyse those samples. A further aspect is that a large number of unique markers may be generated, which can be readout by a microscope and by DNA sequencing like NGS. Thus, embodiments of the present invention can allow for phenomics-2-multi-omics characterisation at scale.

In one aspect, a marker for marking a biological sample or a discrete entity comprising the biological sample is provided. The marker comprises an oligonucleotide nanostructure backbone with a plurality of attachment sites at predetermined positions. Further, the marker comprises a plurality of labels for attachment to at least some of the attachment sites, and at least a first orientation indicator and a second orientation indicator. Each label comprises at least one dye, an encoding oligonucleotide portion configured to encode characteristics of the at least one dye, and an attachment oligonucleotide portion configured to reversibly attach the label to one of the attachment sites. Further the attachment oligonucleotide portion of each label comprises a unique oligonucleotide sequence configured to bind to a complementary sequence of one of the attachment sites.

An oligonucleotide is, for example, a single stranded DNA or RNA molecule, that may be sequenced to determine its sequence of nucleotides. Complementary parts of oligonucleotides may hybridise or bind to each other. In a preferred embodiment, the biological sample comprises at least one cell.

The orientation indicators are configured to attach to the backbone, and may be used to visually determine the orientation of the marker in space. The encoding oligonucleotide portion is a unique sequence of nucleic acids that are unique to the excitation/emission wavelength and/or the fluorescent lifetime of the at least one dye of the label. The marker is thus visually unambiguously identifiable by its unique combination of dyes in each label as well as their specific attachment sites. The same marker is unambiguously identifiable by sequencing the unique encoding oligonucleotide portions and the attachment oligonucleotide portions.

In a preferred embodiment, the discrete entity is comprised of a polymeric compound. The polymeric compound can be polymerised to form the discrete entity. In particular, the polymeric compound can form a hydrogel. The diameter of the discrete entities or hydrogel beads may be in the range of 10 μm to 10 mm. In further preferred embodiments, the ranges can be 10 μm to 100 μm, 50 μm to 250 μm and 500 μm to 5 mm. This enables embedding and culturing of the biological sample in the discrete entity in scaffold-based suspension 3D cell culture, which combines the benefits of 3D suspension cell culture and scaffold-based cell culture.

In a preferred embodiment, the nanostructure backbone comprises scaffold strands, and staple strands configured to bind to the scaffold strands at predetermined positions to fold the scaffold strand into a predetermined shape. The nanostructure backbone may be a DNA-origami. These DNA origami structures may range in size from a few nanometres into the micron range. For the fabrication of such DNA origami-based structures longer DNA molecules (scaffold strands) are folded at precisely identified positions by so called staple strands. The DNA origami may be designed to provide a self-assembly nanostructure backbone of a particular predetermined shape. This enables an easy and reproducible synthesis and assembly of the backbone. Staple strands may be position-selectively functionalised. The positional resolution in this case is limited by the size of a nucleotide, which is in the range of a nanometre or below. This has been exploited in the prior art to generate fluorescent standards, wherein fluorescent dyes are connected to precisely located bands on the DNA origami. These standards are known as “nanoruler” and are used for the calibration of imaging systems like confocal or super resolution microscopes (e.g. STED), for example, as disclosed by US2014/0057805 A1.

The DNA origami provides a scaffold for the labels. In a preferred embodiment, the DNA origami structure comprises at least one scaffold strand and multiple staple strands, wherein the staple strands are complementary to at least parts of the scaffold strand and configured to bring the scaffold strand into a predetermined conformation. In particular, the strands are oligonucleotides. This enables generating nanostructure backbones with predetermined two- or three-dimensional shapes that can self-assemble. Further, this enables the site-specific placement of attachment sites on the backbone.

The attachment sites can be unique nucleic acid sequences, and in a preferred embodiment, of the staple strands. In a preferred embodiment, the labels may be attached to staple strands of the nanostructure backbone at predetermined attachment sites. Since the staple strands are located at predetermined positions the positions of the attachment sites may equally be predetermined. Thus, the attachment site is a unique oligonucleotide sequence complementary to the attachment oligonucleotide portion of one label.

In a preferred embodiment, the largest spatial extent of the nanostructure backbone is in a range from 10 nm to 10000 nm, and in a further preferred embodiment, in a range from 0.1 μm to 5 μm. This enables a particularly compact marker.

In a preferred embodiment, the attachment sites are spaced apart from each other in a range from 1 nm to 2000 nm, and in a further preferred embodiment in a range from 200 nm to 1000 nm. This enables a particularly dense arrangement of labels on the nanostructure backbone. The spacing between the attachment sites may be chosen depending on the resolving power of a readout device used to read out the labels. In further preferred embodiments, the ranges may correspond to the lateral resolution achievable with different microscopic modalities such as for example single molecule localization microscopy (1 nm to 25 nm), structured illumination and STED microscopy (50 nm to 100 nm), high NA (numerical aperture) light microscopy (around 200 nm), and low NA light microscopy (around 500 nm). The labels may be distanced from each other such that the readout device can resolve the labels individually.

In a preferred embodiment, the labels comprise primer sequences configured to enable sequencing of the attachment portion and the encoding portion, and in a preferred embodiment, all labels comprise the same primer sequences. This enables particular efficient sequencing of the portions.

In a preferred embodiment, each label comprises a cleavage site configured to separate the dye from the label. The cleavage site may allow enzymatic, temperature, or light induced cleavage. This enables efficient removal of the dye from portions of the label, particularly prior to sequencing the portions.

In a preferred embodiment, the dye is a fluorophore. In a preferred embodiment, each label has fluorophore(s) with different characteristics, such as at least one of excitation wavelength, emission wavelength and fluorescence lifetime, to enable generating a larger number of different markers. According to a preferred embodiment, the dye is a combination of dyes as described in the patent application with the application number PCT/EP2021/073819, the complete content thereof is incorporated herein by reference.

In a preferred embodiment, the marker comprises an anchor portion configured to attach the marker to a specific biological feature of the biological sample. For example, the anchor portion may be an oligonucleotide (part of the label or part of the nanostructure) configured to attach to a genomic sequence of the biological sample. This enables localisation of the marker in the cell nucleus, for example.

In a preferred embodiment, the nanostructure backbone extends linearly in one dimension and the first orientation indicator and the second orientation indicator are spaced apart from each other, or arranged on opposite ends of the nanostructure backbone. This enables determining the orientation of the marker. The orientation indicators may comprise fluorescent dyes, for example. In particular, the first orientation indicator and the second orientation indicator have different properties, such as excitation wavelength, fluorescence emission wavelength, and/or fluorescence lifetime.

In a preferred embodiment, the nanostructure backbone extends in two dimensions or three dimensions and the nanostructure backbone comprises at least a third orientation indicator. This enables determining the orientation of the marker.

In a further aspect a method is provided for analysing a biological sample comprising the following steps: introducing a plurality of markers (e.g., according to one of the preceding embodiments) into the biological sample or into a discrete entity comprising the biological sample; acquiring at least one optical readout of the biological sample and the markers; determining in the optical readout for at least a first part of the biological sample the individual markers associated with the first part of the sample based on the at least one dye of each of the labels of each marker, in particular on the fluorescent characteristics of each label and its particular attachment site; dissociating the biological sample or the discrete entity into dissociated sample parts and separating the dissociated sample parts; sequencing a genetic content of at least one of the dissociated sample parts together with the encoding oligonucleotide portion and the attachment oligonucleotide portion of the respective associated markers to generate sequencing data; determining in the sequencing data a presence of the sequences of the attachment oligonucleotide portion and the encoding oligonucleotide portion; and correlating the sequencing data to the first part of the biological sample based on the presence of the sequences and the individual markers present in the first part of the sample.

The markers introduced, in a preferred embodiment, differ by their labels and/or the positions of label on nanostructure, that means the particular attachment sites of the labels. The markers may be introduced into the sample fully assembled or they may be assembled in situ. The optical readout is, in a preferred embodiment, an image stack or a 3D image.

Dissociation may comprise removing the discrete entity. The dissociated sample parts may be individual cells or small cell clusters.

This enables linking phenotypic information from the optical readout to genotyping information from the sequencing data.

When the biological sample are embedded in a discrete entity such as a polymeric compound, in particular a hydrogel, the associated markers and the biological sample are kept in close proximity. This enables particularly easy handling of the biological sample with the markers. For further examples of a discrete entity comprising a biological sample and a generalised method for imaging a discrete entity comprising a biological sample, reference is made to the applications PCT/EP2021/058785 and PCT/EP2021/061754, the content of which are full incorporated herein by reference.

The optical readout may be an image-based readout, which may be acquired on a microscope like a point-scanning confocal or a camera-based/widefield imaging system for example a spinning disk microscope, a light sheet fluorescence microscope, a light field microscope, and/or a stereomicroscope. Further, the optical readout may be non-image based readouts for example in a cytometer or a flow-through based readout device with at least one point detector or a line detector. A readout may consist of a discrete readout, for example a single acquisition of an emission spectrum or image stack, a readout may be a readout data stream, for example in a point-scanning confocal or cytometer, which is substantially continuous. Further a readout may be a sequence of images for example a spectral or hyperspectral image stack, wherein in each image fluorescence emission of different wavelength bands is recorded.

The optical readout may be generated by a readout device used to perform fluorescence multi-colour reading or imaging. The readout device typically includes at least one excitation light source, a detection system including at least one detection channel and may further contain filters and/or dispersive optical elements such as prisms and/or gratings to route excitation light to the sample and/or to route emission light from the sample onto to a detector or onto an appropriate area of the detector. The detection system may comprise several detection channels, may be a spectral detector detecting multiple bands of the spectrum in parallel, or a hyperspectral detector detecting a contiguous part of the spectrum. The detection system contains at least one detector, which may be a point-detector (e.g. a photomultiplier, an avalanche diode, a hybrid detector), an array-detector, a camera, hyperspectral camera. The detection system may record intensities per channel as is typically the case in cytometers or may be an imaging detection system that records images as in the case of plate readers or microscopes. A readout device with one detector channel, for example a camera or a photomultiplier, may generate readouts with multiple detection channels using, for example, different excitation and emission bands.

FIG. 1 shows schematically oligonucleotide nanostructure backbones 100, 102, 104, 106, 108 with different geometries. Generally, the nanostructure backbones 100, 102, 104, 106, 108 comprise nucleic acids. In particular, the nanostructure backbones 100, 102, 104, 106, 108 are DNA-origami based, which allows generating predetermined, stable two- and three-dimensional shapes. Further, this allows generating a plurality of attachment sites at predetermined positions along the nanostructure backbones 100, 102, 104, 106, 108. The attachment sites are stretches of oligonucleotide, that are unique and allow the hybridisation of complementary oligonucleotides, for example to attach labels to the nanostructure backbones 100, 102, 104, 106, 108 at these predetermined positions.

Nanostructure backbone 100 is linear or rod-like. It comprises a first orientation indicator 110 and a second orientation indicator 112. The orientation indicators 110, 112 may be used to determine the orientation, directionality or polarity of the nanostructure backbone 100. The orientation indicators 110, 112 may comprise a dye, in particular a fluorescent dye, such as fluorescein or a fluorescent protein. In addition, the dye of the first orientation indicator 110 has different characteristics than the dye of the second orientation indicator 112. The characteristics may include fluorescent emission characteristics, excitation characteristics or lifetime characteristics. This enables differentiating between the first and the second orientation indicators 110, 112 in an optical readout of the nanostructure 100, for example generated by a microscope, a cytometer, or an imaging cytometer. The orientation indicators 110, 112 are arranged spaced apart from each other. In a preferred embodiment, each orientation indicator 110, 112 is arranged on the backbone 100 at opposite ends. Thus, the first and second orientation indicators 110, 112 enable differentiating between a first end and a second end of the backbone 100. Ultimately, this enables determining the orientation, directionality or polarity of the backbone 100, for example from the first orientation indicator 110 on the first end to the second orientation indicator 112 on the second end.

The nanostructure 102 is sheet-like, which may be a large linear DNA molecule or an assembly of multiple DNA molecules. Sheet-like nanostructures may increase the number of available attachment sites substantially. In order to be able to determine the orientation of the nanostructure 102, a third orientation indicator 114 is provided.

Further geometries are possible, for example, the tetrahedral nanostructure 104, the cubic nanostructure 106, or the polyhedral nanostructure 108. These may comprise a fourth orientation indicator 116 in order to determine their orientation.

Figure 2:
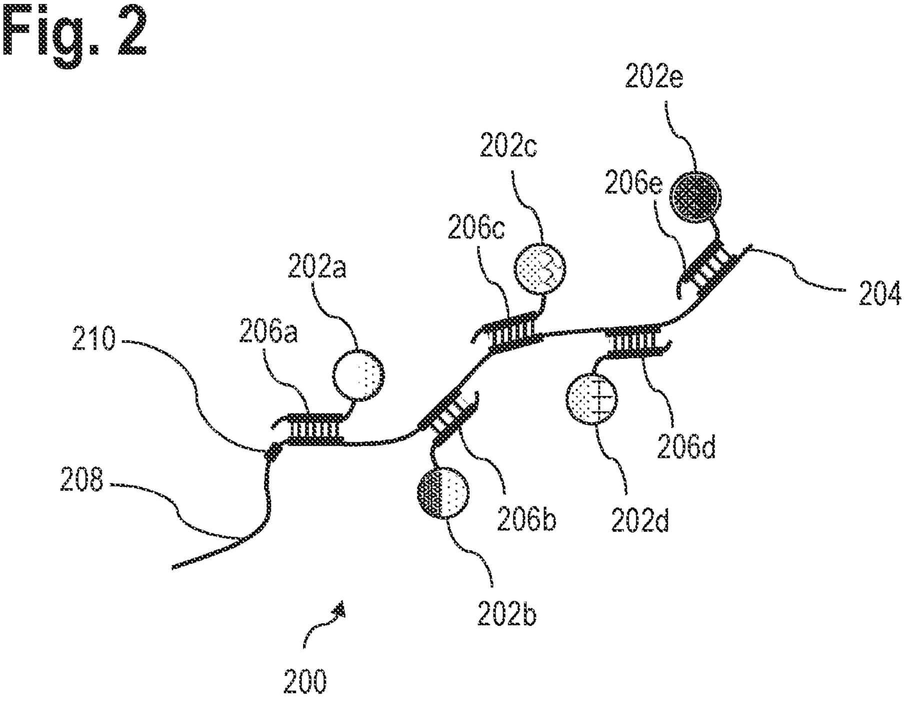
FIG. 2 shows a label for attachment to attachment sites of the nanostructure backbones.

FIG. 2 shows schematically a label 200 for attachment to the attachment sites of the nanostructure backbones 100, 102, 104, 106, 108. The label 200 comprises several fluorescent dyes 202*a*, 202*b*, 202*c*, 202*d*, 202*e*. The fluorescent dyes 202*a* to 202*e* may differ in their fluorescent properties, for example, excitation wavelengths, emission wavelengths and fluorescent lifetime characteristics. In a preferred embodiment, the dyes 202*a* to 202*e* of the label 200 may be individually identified in a read-out in particular of the label 200. Depending on the number of dyes in the used when generating the label 200, a certain number of unique labels can be generated. Typically, the number of different dyes used in total may be in the range of 5-50, for example. For 20 dyes and when using 5 dyes for each label it is easily possible to generate a set of labels with 15,504 unique labels.

The dyes 202*a* to 202*e* are individually attached to a label support 204. The label support 204 may be an oligonucleotide and each of the dyes 202*a* to 202*e* may be specifically attached to the label support 204 via a unique hybridisation part 206*a*, 206*b*, 206*c*, 206*d*, 206*e*. Moreover, the one end 208 of the label support 204 may be specifically attached to the nanostructure backbones 100 to 108, as described in more detail below. A cleavage site 210 is provided to cleave the label support 204. This enables removing the dyes 202*a* to 202*e* from the end 208 of the label support 204, for example, when the label 200 is attached to one of the nanostructure backbones 100 to 108. The orientation indicators 110, 112, 114, 116, in a preferred embodiment, have the same structure as described for the label 200.

Figure 3:
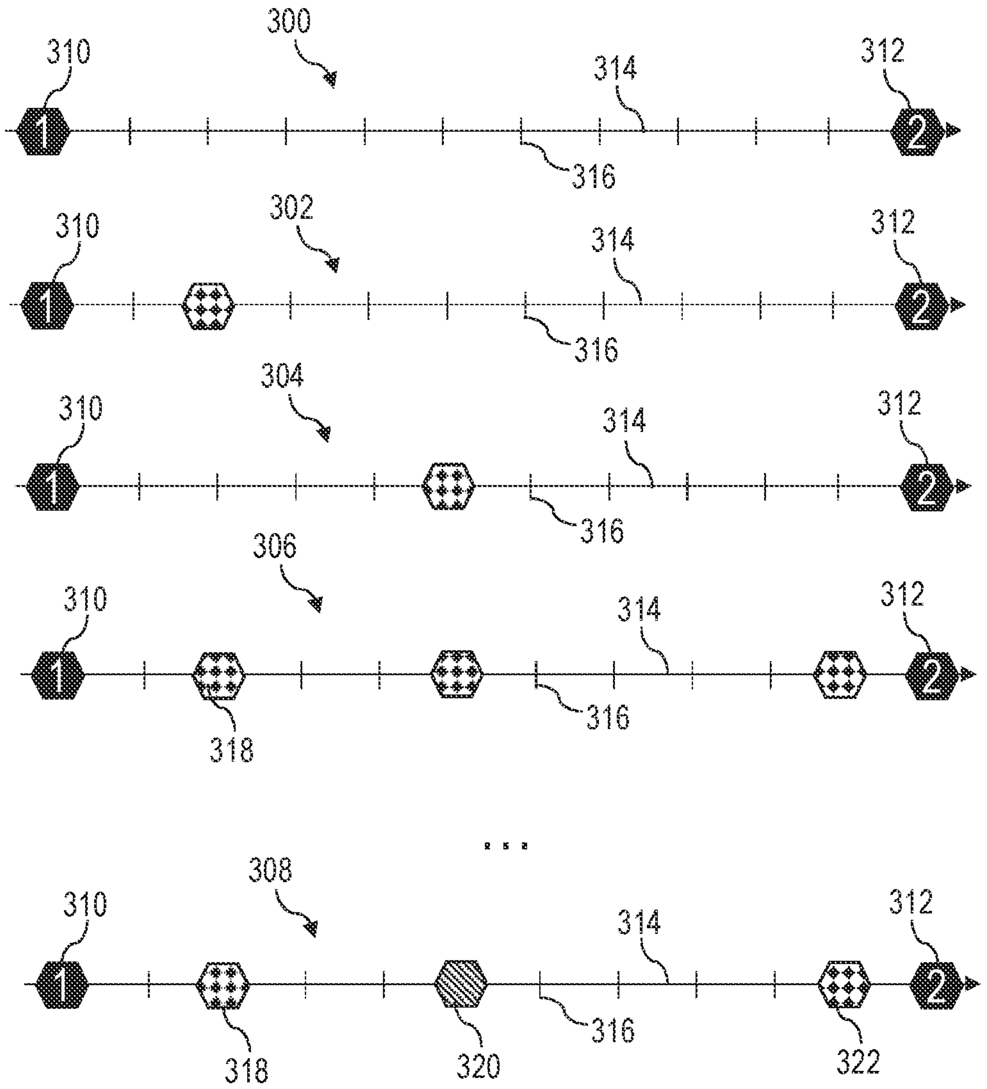
FIG. 3 shows a variety of rod-shaped markers.

FIG. 3 shows schematically a variety of rod-shaped markers 300, 302, 304, 306, 308. The markers 300 to 308 each comprise a first orientation indicator 310 and a second orientation indicator 312, at a first attachment site and a second attachment site of the nanostructure backbone 314, respectively. In addition, there are ten further attachment sites, one of which is indicated by reference sign 316. In case of the marker 308, labels 318, 320, 322 are attached at three further attachment sites 316. The attachment sites 316 of each nanostructure backbone 314 is unique such that the labels 318, 320, 322 are specifically attachable to a particular attachment site 316. The markers 300, 302, 304, 306, 308 are, in a preferred embodiment, between 1 to 2 μm in length.

The orientation indicators 310, 312 generate a relative coordinate system for the markers 300, 302, 304, 306, 308, on which each attachment site 316 may be placed. For example, each attachment site 316 may be assigned an index n with n=1, 2, 3, . . . , based on the unique location of the respective attachment site 316. Thus, the different markers 300 to 308 can all be distinguished visually, due to their use of labels with differing properties and/or the labels being attached at different, distinguishable attachment sites 316 along the nanostructure backbone 314.

Figure 4:
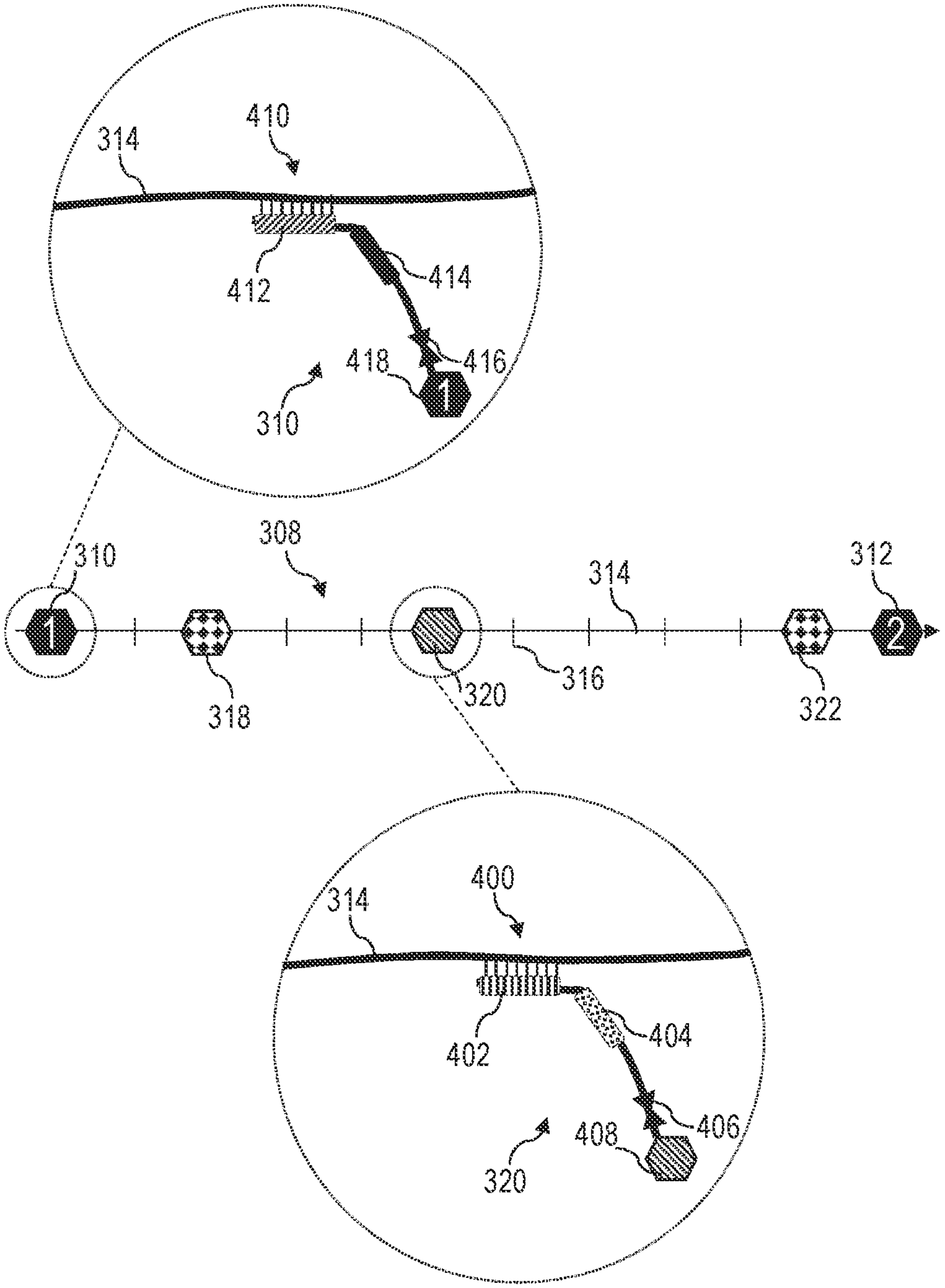
FIG. 4 shows details of a rod-shaped marker.

FIG. 4 shows schematically details of the rod-shaped marker 308, in particular, the label 320 and its attachment to the nanostructure backbone 314. The label 320 is attached to the nanostructure backbone 314 at a particular attachment site 400 of the nanostructure backbone 314. This attachment site 400 has a unique oligonucleotide sequence that allows hybridisation of a complementary attachment oligonucleotide portion 402 of the label 320. Thus, each attachment site of the marker 308 has a unique oligonucleotide sequence enabling to specifically target labels for each one of the attachment sites.

In addition, the label 320 comprises an encoding oligonucleotide portion 404. The encoding portion 404 is an oligonucleotide sequence that is unique to the fluorescent dye or dyes 408 the label 320. This means that the dyes of a particular label may be identified by the sequence of the encoding portion.

The label 320 also comprises a cleavage site 406 for removing the dye 408 from the encoding portion 404 and the attachment portion 402.

Thus, each label has a unique sequence for the particular dyes (e.g. the encoding portion 404) and a further unique sequence that hybridises to a particular one of the attachment sites of a nanostructure backbone (e.g. the attachment portion 402).

The first and second orientation indicators 310, 312 are similarly constructed. For example, the orientation indicator 310 is attached to an attachment site 410 of the nanostructure backbone 314 by a unique complementary attachment oligonucleotide portion 412. Further, the orientation indictor 310 comprises an encoding portion 414, that is unique to the dye or dyes 418 of the orientation indicator. The dyes 418 may be removed from the encoding portion 414 and the attachment portion 412 by cleaving a cleavage site 416.

Figure 5:
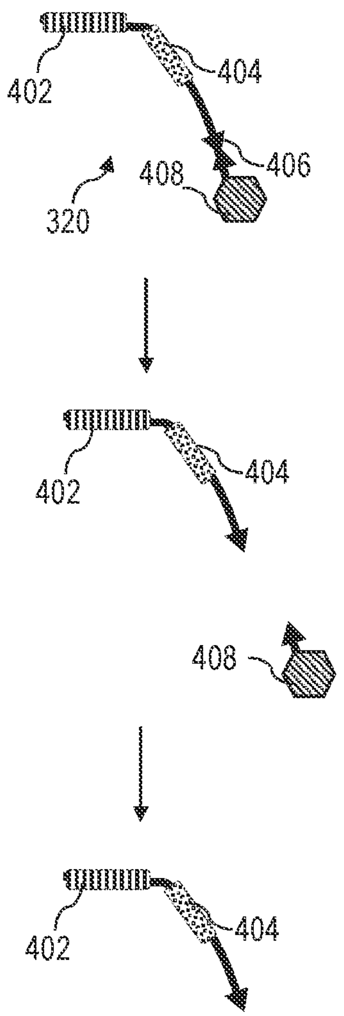
FIG. 5 shows steps for preparing a label for sequencing.

FIG. 5 shows steps for preparing the label 320 for sequencing, for example, to read the information of the attachment portion 402 and the encoding portion 404. Initially, the label 320 is removed from the nanostructure backbone by heating to melt the hybridised attachment portion 402 off the nanostructure backbone. Next the dyes 408 are removed from the label 320 by cleaving the cleavage site 406, for example, by enzymatic cleavage in case the cleavage site 406 is a restriction site. Alternatively, the cleavage site 406 may be cleaved by light or temperature. The remaining attachment portion 402 and encoding portion 404 may be separated, for example, by chromatography and subsequently sequenced. To that end, universal primers may be ligated to the remaining attachment portion 402 and encoding portion 404. Alternatively, the universal primers may be provided with the label support.

Figure 6:
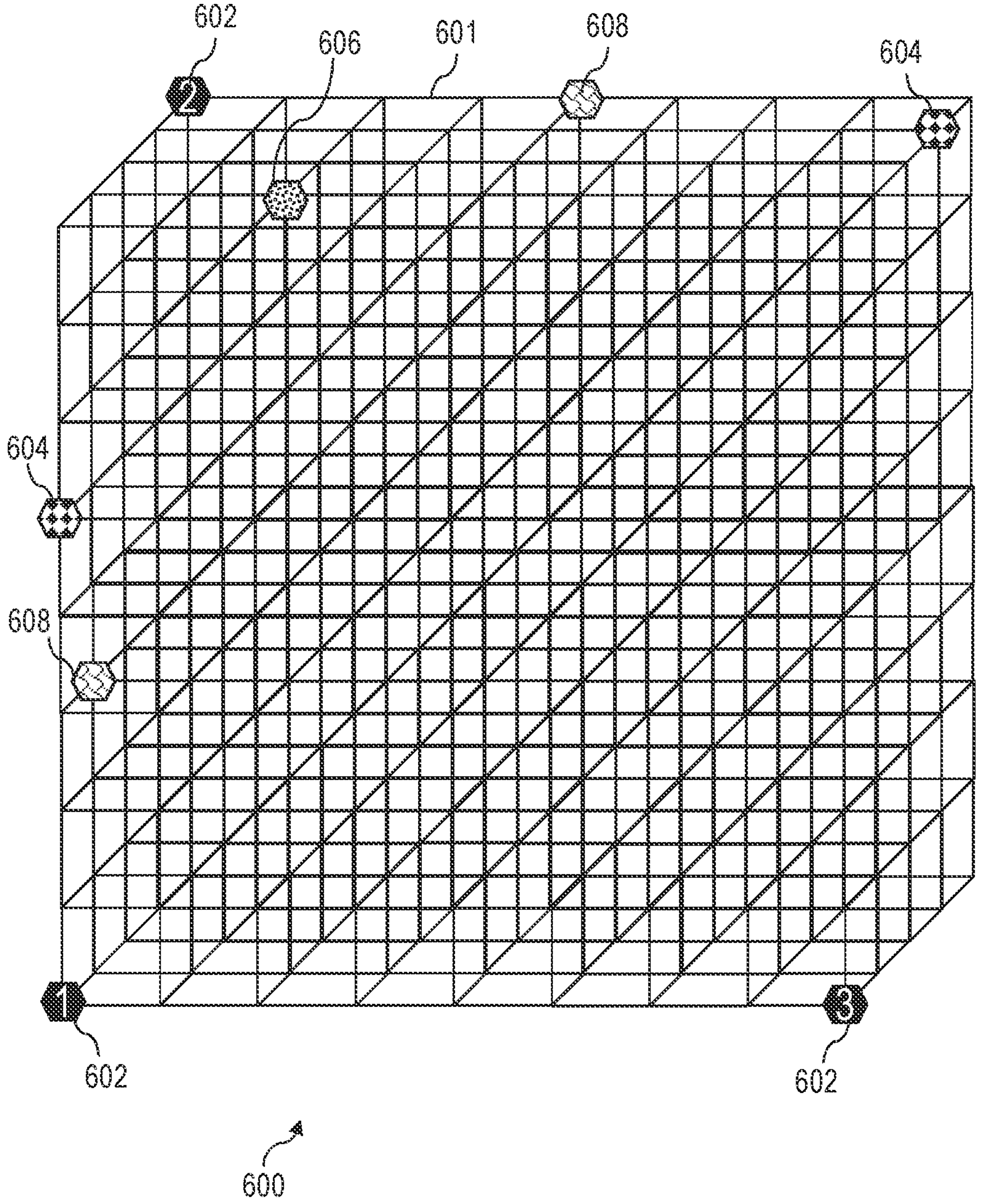
FIG. 6 shows a cube-shaped marker.

FIG. 6 shows schematically an example of a cube-shaped marker 600 with a three-dimensional array nanostructure backbone 601. The marker 600 comprises three orientation indicators 602. Further, the marker 600 comprises a set of different labels 604, 606, 608. Each label 604, 606, 608 is attached at a particular attachment site of the marker 600. The attachment sites may, for example, be at the corners or edges of the array of the backbone 601. The labels 604, 606, 608 differ in their fluorescent properties, such as fluorescent lifetime, emission wavelength and excitation wavelength.

Thus, similarly to the markers 300 to 308 in FIG. 3, the marker 600 may be distinguished from other markers in an optical read-out by the placement of particular labels at specific attachment sites of the backbone 601. In comparison to the rod-shaped markers 300 to 308, the cube-shaped marker 600 provides for around 360 attachment sites for labels, which increases the number of possible combinations of labels and their position on the backbone 601. The physical size of the cube-shaped marker 600 is in the range of 2.5 to 10 μm per side of the cube.

Figure 7:
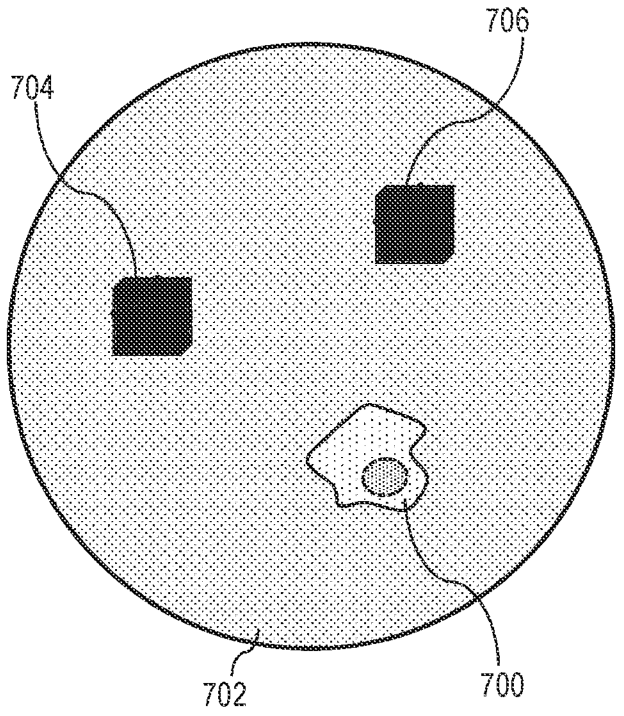
FIG. 7 shows a discrete entity with a biological sample and markers.

FIG. 7 shows schematically a biological sample 700 embedded in a discrete entity 702. The discrete entity 702 may be a hydrogel bead. The discrete entity 702 further comprises a cube-shaped markers 704, 706. The markers 704, 706 may be similar in structure to the marker 600. However, the markers 704, 706 may differ from each other in the specific labels attached to the respective backbone and/or in the specific attachment sites the labels are attached to. The biological sample 700 may be a single cell, for example.

Figure 8:
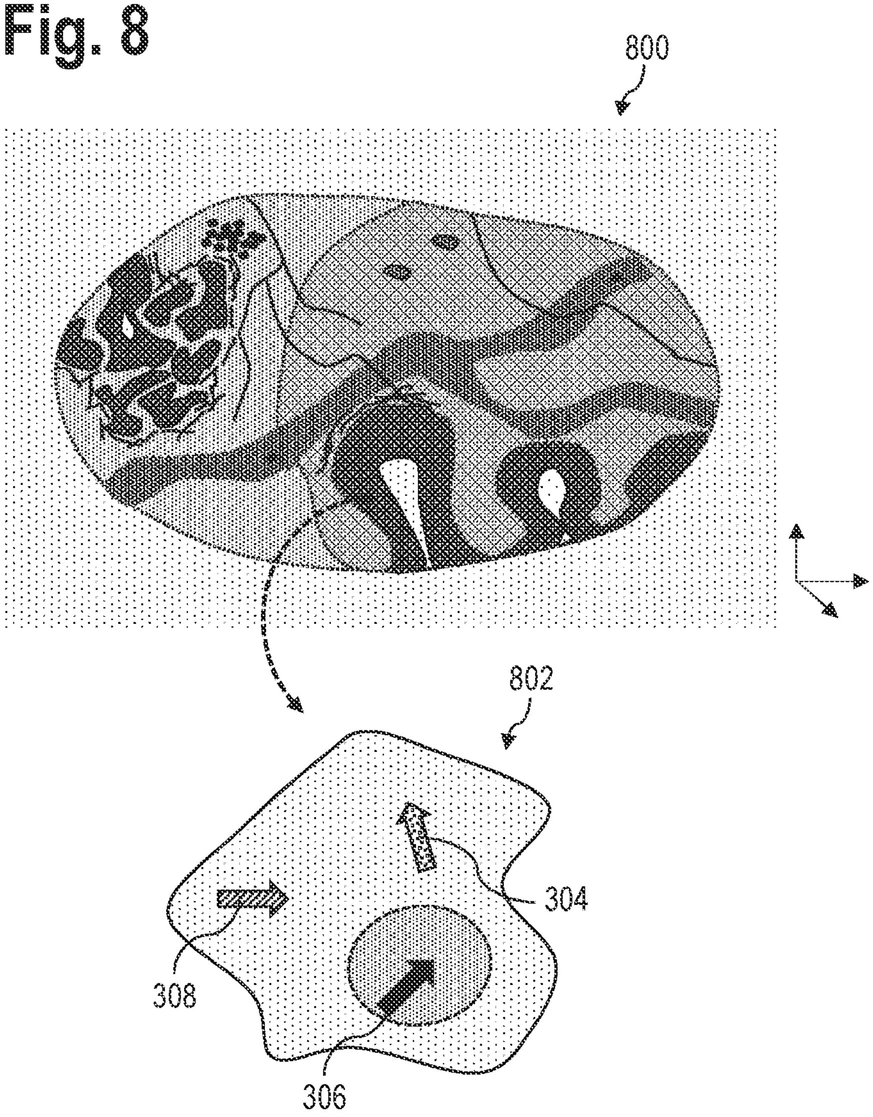
FIG. 8 shows a biological sample with markers.

FIG. 8 shows schematically a biological sample 800. The sample 800 may be a section from a biopsy, for example, comprising a plurality of tissues and/or cells. The sample 800 may be stained with a plurality of markers, including the markers 304, 306, 308. As an example, a cell 802 of an intestinal part 804 of the biological sample 800 is described in more detail. The markers 304, 306, 308, represented here by their directionality as arrows, are introduced into the cell 802. By using a plurality of markers, each cell of interest in the sample 800 may be stained by a unique combination of markers.

With reference to FIGS. 7 and 8, the cell 700 and the cell 802 may be one of a larger group of cells. In the case of the sample 800 and the cell 802, the entire sample 800 may be stained with markers and therefore each cell of the plurality of cells the sample 800 is made up of may be stained by a unique combination of markers. The cell 802 may be one of a larger group of cells, each cell individually embedded in a discrete entity with a unique combination of markers. Thus, the markers enable identifying cells 700, 802 visually in optical readouts of the discrete entity 702 or the sample 800.

Figure 9:
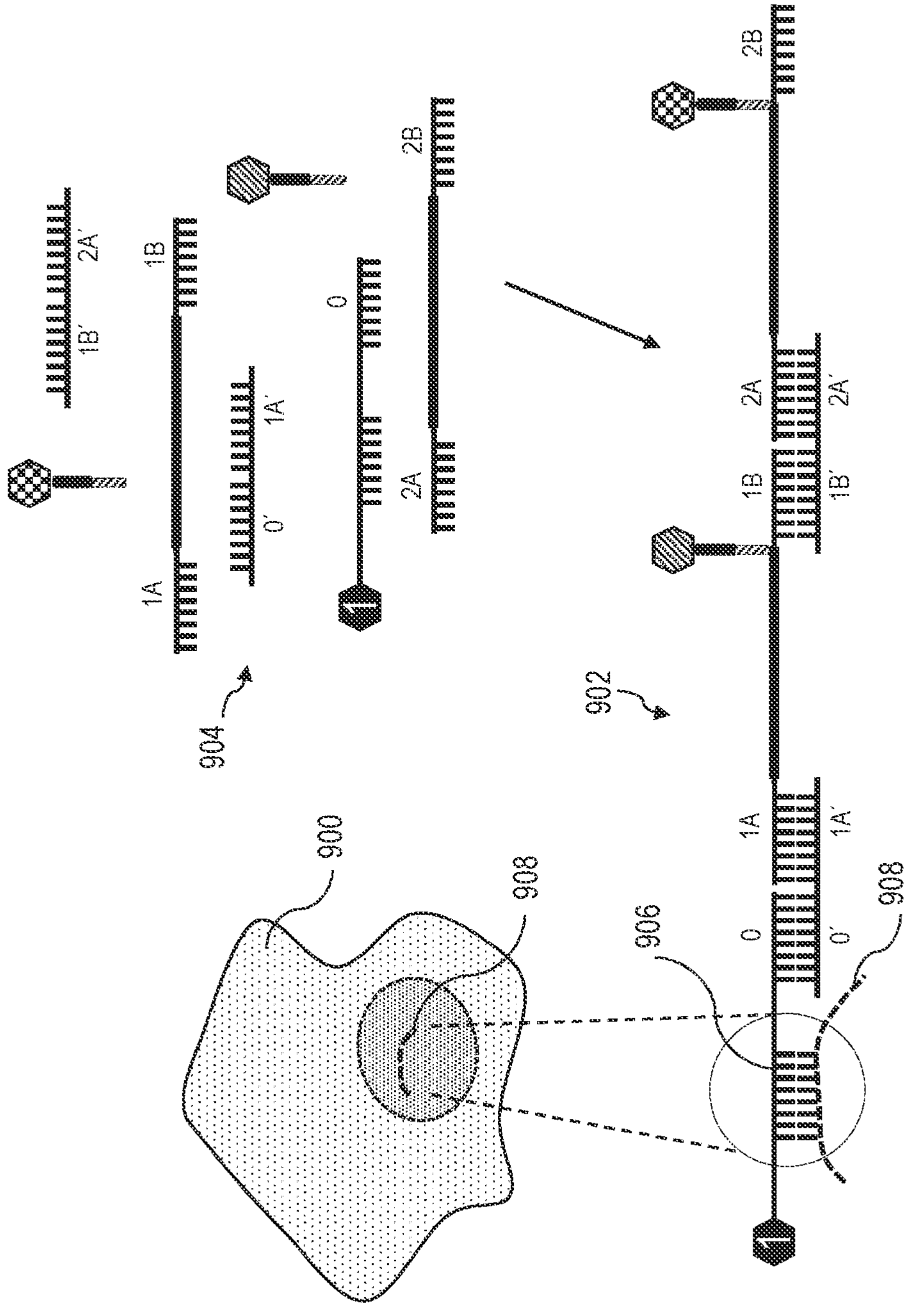
FIG. 9 shows the assembly of a marker.

FIG. 9 shows schematically a preferred embodiment of a method of staining a biological sample 900 with markers. Instead of introducing assembled markers into a biological sample, the markers may be assembled in situ. Exemplarily, the assembly of part of a marker 902 is shown. To that end, individual parts 904 of the marker 902 are introduced into the sample 900. The individual parts 904 may include staple strands and scaffold strands of the DNA-origami backbone of the marker 902, as well as the orientation indicators and the labels. Since each of the individual parts 904 of the marker 902 is smaller than the marker 902, the individual parts 904 are easier to introduce into the sample 900. The individual parts 904 of the marker 902 then hybridise at complementary oligonucleotide portions as indicated by the alpha-numeric notation of the individual parts 904.

Optionally, the marker 902, in particular its nanostructure backbone, may comprise an anchor portion 906. The anchor portion 906 is an oligonucleotide sequence that is complementary to a genetic sequence 908 of the biological sample 900. For example, the biological sample 900 may be a cell and the genetic sequence 908 is part of the genome of the cell. This allows anchoring the marker 902 inside the sample 900.

Figure 10:
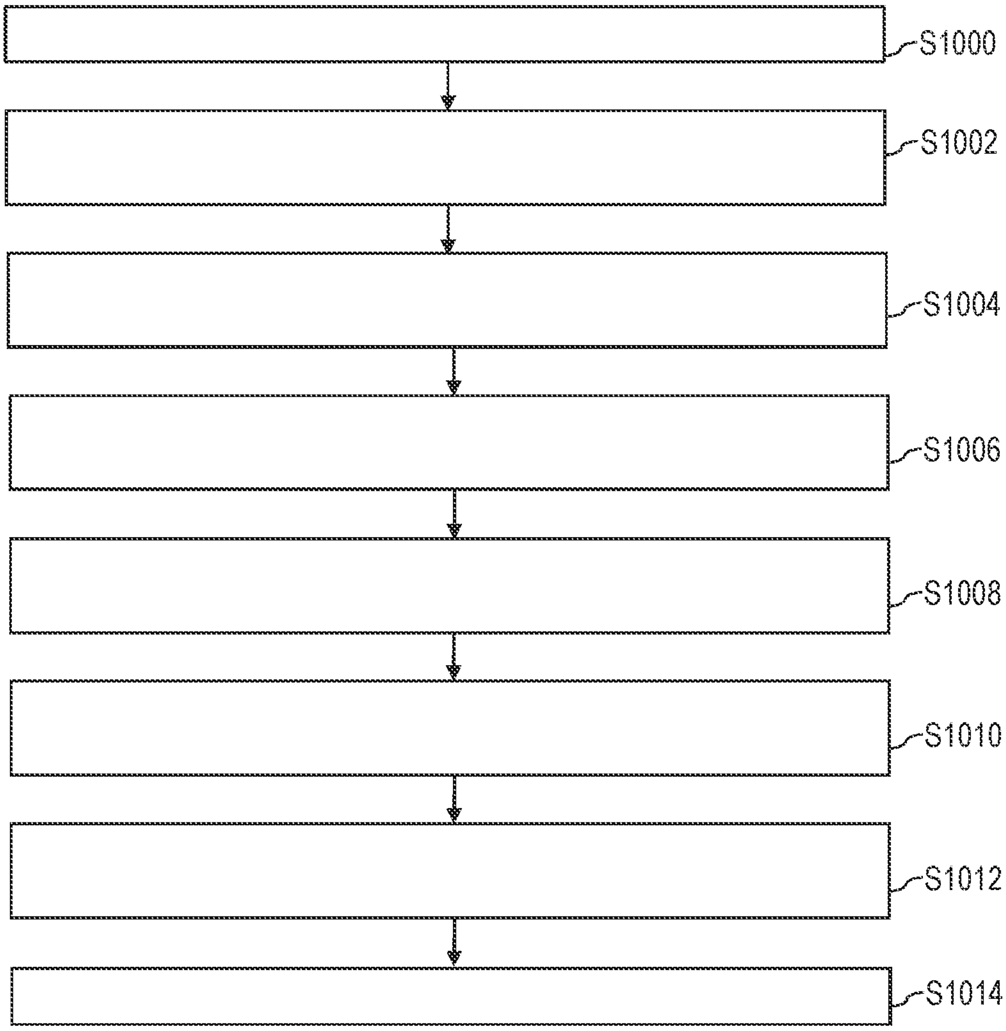
FIG. 10 shows a flow chart of a method for analysing a biological sample.

FIG. 10 shows a flow chart of a method for analysing a biological sample. The biological sample is, in a preferred embodiment, a tissue, in particular a tissue section (as shown in FIG. 8). Alternatively, the biological sample is embedded in a discrete entity, particularly a hydrogel bead, in which case the biological sample may be a single cell (as shown in FIG. 7).

In a first step S1000, the biological sample is stained. This may include the introduction of a plurality of markers into the sample or the introduction of the individual parts of a plurality of markers for in situ assembly. The plurality of markers is generated with a plurality of labels with different fluorescent properties that are attached at predetermined attachment sites. This allows generating a large variety of distinguishable markers.

In case the biological sample is embedded in a discrete entity, the discrete entity may be stained instead or in addition of the biological sample. The markers may be introduced into the discrete entity when the discrete entity is formed during embedding the biological sample in the discrete entity.

In step S1002, an optical readout, in a preferred embodiment an image or an image stack, of the biological sample together with the markers is generated. In case the biological sample is embedded in the discrete entity, the discrete entity may be imaged together with the biological sample and the markers.

In step S1004, the optical readout is analysed to determine the markers associated with at least a first part of the biological sample. The markers may each be identified by the particular labels attached to the particular attachment sites. This includes the fluorescent properties of the dyes of the labels. In case the markers were introduced into the biological sample the markers associated with the biological sample are the markers within the biological sample. In case the biological sample is embedded in a discrete entity, the associated markers are the markers within the discrete entity.

In step S1006, the biological sample is dissociated. This is to generate dissociated sample parts, which are separated subsequently. In case the biological sample is a tissue section, the dissociated sample parts may be individual cells or small cell clusters. In case the biological sample is embedded in a discrete entity, the discrete entity may be dissolved.

In step S1008, the genetic content of least one of the dissociated biological sample parts is sequenced together with the encoding oligonucleotide portion and the attachment oligonucleotide portion of the respective markers associated with the particular biological sample part. This generates sequence data comprising sequences of the encoding oligonucleotide portion and the attachment oligonucleotide portion as well as the genetic content.

In step S1010, the presence of the sequence of the attachment oligonucleotide portions and the sequence of the encoding portions is determined in the sequencing data. This enables determining the presence of respective markers in the dissociated sample part.

In step S1012, the sequencing data is correlated to the first part of the biological sample based on the presence of the sequences and the individual markers present in the first part of the sample. For each marker it is known which labels are attached at which attachment sites, therefore, in the optical readout, the markers present may be identified unambiguously. In the sequencing the identity of the markers present in the sequenced sample can be likewise identified by determining the presence of the respective encoding and attachment oligonucleotide sequences. By comparing these, an optical readout of a sample with particular markers may be correlated or assigned to sequencing data of that sample containing these particular markers. This enables directly linking data about the phenotype in the optical readout with data about the genotype in the sequencing data. The method ends in step S1014.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS

| | |
|---|---|
| 100, 102, 104, 106, 108, 314, 601 | Nanostructure backbone |
| 110, 112, 114, 310, 312, 602 | Orientation indicator |
| 200, 318, 320, 322, 604, 606, 608 | Label |
| 202a, 202b, 202c, 202d, 202e, 408, 418 | Fluorescent dye |
| 204 | Label support |
| 206a, 206b, 206c, 206d, 206e | Hybridisation part |
| 208 | End of label support |
| 210, 406, 416 | Cleavage site |
| 300, 302, 304, 306, 308, 600, 704, 706, 902 | Marker |
| 316, 400, 410 | Attachment site |
| 402, 412 | Attachment oligonucleotide portion |
| 404, 414 | Encoding oligonucleotide portion |
| 700, 800, 900 | Biological sample |
| 702 | Discrete entity |
| 802 | Cell |
| 904 | Individual parts of a marker |
| 906 | Anchor portion |
| 908 | Genetic sequence |

The invention claimed is:

1. A marker for marking a biological sample or a discrete entity comprising the biological sample, the marker comprising:
- an oligonucleotide nanostructure backbone with a plurality of attachment sites at predetermined positions,
- a plurality of labels for attachment to at least one of the attachment sites, and
- at least a first orientation indicator and a second orientation indicator,
- wherein each respective label comprises at least one dye, an encoding oligonucleotide portion configured to encode characteristics of the at least one dye, and an attachment oligonucleotide portion configured to reversibly attach to one of the attachment sites, and
- wherein the attachment oligonucleotide portion of each label comprises a first unique oligonucleotide sequence configured to bind to a complementary sequence of the one of the attachment sites, and the encoding oligonucleotide portion of each label comprises a second unique oligonucleotide sequence that is unique to the at least one dye.

2. The marker according to claim 1, wherein the oligonucleotide nanostructure backbone comprises scaffold strands and staple strands configured to bind to the scaffold strands at predetermined staple strand positions to fold the scaffold strands into a predetermined shape.

3. The marker according to claim 2, wherein the staple strands comprise the plurality of attachment sites.

4. The marker according to claim 1, wherein a largest spatial extent of the oligonucleotide nanostructure backbone is in a range from 10 nm to 10000 nm.

5. The marker according to claim 4, wherein a largest spatial extent of the oligonucleotide nanostructure backbone is in a range from 0.1 μm to 5 μm.

6. The marker according to claim 1, where the plurality of attachment sites are spaced apart from each other in a range from 1 nm to 2000 nm.

7. The marker according to claim 6, where the plurality of attachment sites are spaced apart from each other in a range from 200 nm to 1000 nm.

8. The marker according to claim 1, wherein the plurality of labels comprise primer sequences configured to enable sequencing of the attachment oligonucleotide portion and the encoding oligonucleotide portion.

9. The marker according to claim 8, wherein all labels of the plurality of labels comprise the same primer sequences.

10. The marker according to claim 1, wherein each label comprises a cleavage site configured to separate the at least one dye from the label.

11. The marker according to claim 1, wherein the at least one dye is a fluorophore.

12. The marker according to claim 1, comprising an anchor portion configured to attach the marker to a specific biological feature of the biological sample.

13. The marker according to claim 1, wherein the oligonucleotide nanostructure backbone extends linearly in one dimension and the first orientation indicator and the second orientation indicator are spaced apart from each other, or arranged on opposite ends of the oligonucleotide nanostructure backbone.

14. The marker according to claim 1, wherein the oligonucleotide nanostructure backbone extends in two dimensions or three dimensions and the oligonucleotide nanostructure backbone comprises at least a third orientation indicator.

15. The marker according to claim 1, wherein each of the first orientation indicator and the second orientation indicator is configured to attach to the oligonucleotide nanostructure backbone, and wherein the first orientation indicator and the second orientation indicator are configured for visually determining an orientation of the marker.

16. A method for analysing a biological sample comprising the following steps:
- introducing a plurality of markers according to claim 1 into the biological sample or into a discrete entity comprising the biological sample,
- acquiring at least one optical readout of the biological sample and the plurality of markers,
- determining in the optical readout for at least a first part of the biological sample the individual markers of the plurality of markers associated with the first part of the biological sample based on the at least one dye of each of the labels of each marker of the plurality of markers, dissociating the biological sample or the discrete entity into dissociated sample parts and separating the dissociated sample parts, sequencing a genetic content of at least one of the dissociated sample parts together with the encoding oligonucleotide portion and the attachment oligonucleotide portion of the respective associated markers of the plurality of markers to generate sequencing data, determining in the sequencing data a presence of sequences of the attachment oligonucleotide portion and the encoding oligonucleotide portion, and correlating the sequencing data to the first part of the biological sample based on the presence of the sequences and the individual markers present in the first part of the sample.

* * * * *